US008558051B2

United States Patent
Toshishige et al.

(10) Patent No.: US 8,558,051 B2
(45) Date of Patent: Oct. 15, 2013

(54) DISPOSABLE ABSORBENT ARTICLE HAVING ODOR CONTROL SYSTEM

(75) Inventors: Hiroshi Toshishige, Chuo-ku (JP); Tomoko Okuda, Ikoma (JP); Yukio Heki, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 409 days.

(21) Appl. No.: 12/173,061

(22) Filed: Jul. 15, 2008

(65) Prior Publication Data

US 2009/0024101 A1    Jan. 22, 2009

Related U.S. Application Data

(60) Provisional application No. 60/961,029, filed on Jul. 18, 2007.

(51) Int. Cl.
*A61F 13/15*    (2006.01)
*A61F 13/20*    (2006.01)

(52) U.S. Cl.
USPC .......................... 604/359; 604/360; 604/367

(58) Field of Classification Search
USPC .............. 604/359–360, 367, 385.28
See application file for complete search history.

(56) References Cited

U.S. PATENT DOCUMENTS

| | | | |
|---|---|---|---|
| 3,340,875 A | 9/1967 | Elizabeth et al. | |
| 3,563,243 A | 2/1971 | Lindquist | |
| 3,812,044 A | 5/1974 | Connor et al. | |
| 3,860,003 A | 1/1975 | Buell | |
| 3,911,173 A | 10/1975 | Sprague, Jr. | |
| 3,929,135 A | 12/1975 | Thompson | |
| 3,986,972 A | 10/1976 | Loffelman et al. | |
| 4,289,513 A | 9/1981 | Brownhill et al. | |
| 4,324,246 A | 4/1982 | Mullane et al. | |
| 4,342,314 A | 8/1982 | Radel et al. | |
| 4,356,190 A | 10/1982 | Kraskin | |

(Continued)

FOREIGN PATENT DOCUMENTS

| | | |
|---|---|---|
| EP | 348878 A2 | 1/1990 |
| EP | 510619 A1 | 10/1992 |

(Continued)

OTHER PUBLICATIONS

Kirk Okmer, *Encyclopedia of Chemical Technology, Fourth Edition*, 17, pp. 27-90 and 63-82 (1982).

(Continued)

*Primary Examiner* — Michele M Kidwell
(74) *Attorney, Agent, or Firm* — Matthew P. Fitzpatrick; Richard L. Alexander; Abbey A. Lopez

(57) ABSTRACT

A disposable absorbent article comprises a topsheet; a backsheet combined with the topsheet; a fluid storage layer disposed between the topsheet and the backsheet and adjacent to the backsheet; an intermediate layer disposed between the fluid storage layer and the topsheet. The intermediate layer has a body-facing surface and a garment-facing surface. The disposable absorbent article comprises an odor control system. The odor control system comprises an antimicrobial material disposed between the topsheet and the body-facing surface of the intermediate layer; an odor masking material disposed between the backsheet and the garment-facing surface of the intermediate layer; and an odor absorbing and/or adsorbing material disposed in the fluid storage layer. The antimicrobial material and the odor masking material are separated by the intermediate layer.

9 Claims, 3 Drawing Sheets

(56) References Cited

U.S. PATENT DOCUMENTS

| | | | |
|---|---|---|---|
| 4,412,934 A | 11/1983 | Chung et al. | |
| 4,430,243 A | 2/1984 | Bragg | |
| 4,463,045 A | 7/1984 | Ahr et al. | |
| 4,547,195 A | 10/1985 | Jackson | |
| 4,554,292 A | 11/1985 | Lambert et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,634,551 A | 1/1987 | Burns et al. | |
| 4,673,402 A | 6/1987 | Weisman et al. | |
| 4,695,278 A | 9/1987 | Lawson | |
| 4,704,115 A | 11/1987 | Buell | |
| 4,728,455 A | 3/1988 | Rerek | |
| 4,740,520 A | 4/1988 | Hallenbach et al. | |
| 4,785,996 A | 11/1988 | Ziecker et al. | |
| 4,795,454 A | 1/1989 | Dragoo | |
| 4,810,410 A | 3/1989 | Diakun et al. | |
| 4,834,735 A | 5/1989 | Alemany et al. | |
| 4,842,666 A | 6/1989 | Werenicz | |
| 4,888,231 A | 12/1989 | Angstadt | |
| 4,892,536 A | 1/1990 | Desmarais et al. | |
| 4,900,317 A | 2/1990 | Buell | |
| 4,915,854 A | 4/1990 | Mao et al. | |
| 4,940,464 A | 7/1990 | Van Gompel et al. | |
| 4,950,254 A | 8/1990 | Andersen et al. | |
| 4,966,923 A | 10/1990 | Banks et al. | |
| 4,988,344 A | 1/1991 | Reising et al. | |
| 4,988,345 A | 1/1991 | Reising | |
| 4,990,147 A | 2/1991 | Freeland | |
| 5,004,558 A | 4/1991 | Dyroff et al. | |
| 5,006,394 A * | 4/1991 | Baird | 428/138 |
| 5,037,416 A | 8/1991 | Allen et al. | |
| 5,085,654 A | 2/1992 | Buell | |
| 5,092,861 A | 3/1992 | Nomura et al. | |
| 5,114,606 A | 5/1992 | Van Vliet et al. | |
| 5,114,611 A | 5/1992 | Van Kralingen et al. | |
| 5,130,045 A | 7/1992 | Mitchell et al. | |
| 5,132,431 A | 7/1992 | Fuchs et al. | |
| 5,147,345 A | 9/1992 | Young et al. | |
| 5,151,092 A | 9/1992 | Buell et al. | |
| 5,153,161 A | 10/1992 | Kerschner et al. | |
| 5,194,416 A | 3/1993 | Jureller et al. | |
| 5,221,274 A | 6/1993 | Buell et al. | |
| 5,227,084 A | 7/1993 | Martens et al. | |
| 5,234,423 A | 8/1993 | Alemany et al. | |
| 5,244,594 A | 9/1993 | Favre et al. | |
| 5,246,433 A | 9/1993 | Hasse et al. | |
| 5,246,612 A | 9/1993 | Van Dijk et al. | |
| 5,246,620 A | 9/1993 | Gethoffer et al. | |
| 5,246,621 A | 9/1993 | Favre et al. | |
| 5,256,779 A | 10/1993 | Kerschner et al. | |
| 5,260,345 A | 11/1993 | Desmarais et al. | |
| 5,269,775 A | 12/1993 | Freeland et al. | |
| 5,274,147 A | 12/1993 | Kerschner et al. | |
| 5,279,757 A | 1/1994 | Gethoffer et al. | |
| 5,280,117 A | 1/1994 | Kerschner et al. | |
| 5,284,944 A | 2/1994 | Madison et al. | |
| 5,342,338 A | 8/1994 | Roe | |
| 5,360,569 A | 11/1994 | Madison et al. | |
| 5,370,826 A | 12/1994 | Madison et al. | |
| RE34,920 E | 4/1995 | Aziz et al. | |
| 5,405,412 A | 4/1995 | Willey et al. | |
| 5,405,413 A | 4/1995 | Willey et al. | |
| 5,442,066 A | 8/1995 | Madison et al. | |
| 5,460,747 A | 10/1995 | Gosselink et al. | |
| 5,478,357 A | 12/1995 | Madison et al. | |
| 5,482,515 A | 1/1996 | Madison et al. | |
| 5,492,751 A | 2/1996 | Butt, Sr. et al. | |
| 5,503,639 A | 4/1996 | Willey et al. | |
| 5,523,434 A | 6/1996 | Burns et al. | |
| H1579 H * | 8/1996 | Furio | 502/402 |
| 5,550,256 A | 8/1996 | Madison et al. | |
| 5,554,145 A | 9/1996 | Roe et al. | |
| 5,562,646 A | 10/1996 | Goldman et al. | |
| 5,569,234 A | 10/1996 | Buell et al. | |
| 5,570,760 A | 11/1996 | Lai | |
| 5,576,282 A | 11/1996 | Miracle et al. | |
| 5,578,136 A | 11/1996 | Taylor et al. | |
| 5,580,411 A | 12/1996 | Nease et al. | |
| 5,584,888 A | 12/1996 | Miracle et al. | |
| 5,595,967 A | 1/1997 | Miracle et al. | |
| 5,597,936 A | 1/1997 | Perkins et al. | |
| 5,599,335 A | 2/1997 | Goldman et al. | |
| 5,607,760 A | 3/1997 | Roe | |
| 5,609,587 A | 3/1997 | Roe | |
| 5,628,047 A | 5/1997 | Hiroyoshi | |
| 5,635,191 A | 6/1997 | Roe et al. | |
| 5,643,588 A | 7/1997 | Roe et al. | |
| 5,654,421 A | 8/1997 | Taylor et al. | |
| 5,669,844 A | 9/1997 | Homan et al. | |
| 5,686,014 A | 11/1997 | Baillely et al. | |
| 5,686,015 A | 11/1997 | Willey et al. | |
| 5,686,401 A | 11/1997 | Willey et al. | |
| 5,695,679 A | 12/1997 | Christie et al. | |
| 5,698,504 A | 12/1997 | Christie et al. | |
| 5,703,030 A | 12/1997 | Perkins et al. | |
| 5,718,614 A | 2/1998 | Armond et al. | |
| 5,739,327 A | 4/1998 | Arbogast et al. | |
| 5,741,437 A | 4/1998 | Arbogast et al. | |
| H1732 H * | 6/1998 | Johnson | 428/68 |
| 5,769,833 A * | 6/1998 | Hasse | 604/359 |
| 5,769,838 A | 6/1998 | Buell et al. | |
| 5,877,315 A | 3/1999 | Deline et al. | |
| 5,894,896 A | 4/1999 | Smith et al. | |
| 5,897,545 A | 4/1999 | Kline et al. | |
| 5,899,895 A | 5/1999 | Robles et al. | |
| 5,916,661 A | 6/1999 | Benson et al. | |
| 5,941,864 A | 8/1999 | Roe | |
| 5,957,908 A | 9/1999 | Kline et al. | |
| 5,958,289 A | 9/1999 | Arbogast et al. | |
| 5,968,025 A | 10/1999 | Roe et al. | |
| 5,998,350 A | 12/1999 | Burns et al. | |
| 6,004,306 A | 12/1999 | Robles et al. | |
| 6,017,464 A | 1/2000 | Deline | |
| 6,063,750 A | 5/2000 | Loffler et al. | |
| 6,107,539 A | 8/2000 | Palumbo et al. | |
| 6,118,041 A | 9/2000 | Roe et al. | |
| 6,120,487 A | 9/2000 | Ashton | |
| 6,120,489 A | 9/2000 | Johnson et al. | |
| 6,133,216 A | 10/2000 | Loffler et al. | |
| 6,140,294 A | 10/2000 | Delroisse et al. | |
| 6,287,580 B1 | 9/2001 | Gott et al. | |
| 6,302,921 B1 | 10/2001 | Delroisse et al. | |
| 6,414,215 B1 | 7/2002 | Roe | |
| 6,476,288 B1 | 11/2002 | Vanrijswijck et al. | |
| 6,545,147 B1 | 4/2003 | Seebach et al. | |
| 6,545,197 B1 | 4/2003 | Muller et al. | |
| 6,627,786 B2 | 9/2003 | Roe et al. | |
| 6,627,787 B1 | 9/2003 | Roe et al. | |
| 6,680,422 B2 | 1/2004 | Roe | |
| 6,790,798 B1 | 9/2004 | Suzuki et al. | |
| 7,883,495 B2 | 2/2011 | Nonnenmann et al. | |
| 2003/0233082 A1 | 12/2003 | Kline et al. | |
| 2004/0097895 A1 | 5/2004 | Busam et al. | |
| 2004/0122387 A1 | 6/2004 | Long et al. | |
| 2004/0158212 A1 | 8/2004 | Ponomarenko et al. | |
| 2004/0158213 A1 | 8/2004 | Ponomarenko et al. | |
| 2004/0158214 A1 | 8/2004 | Ponomarenko et al. | |
| 2006/0292091 A1 | 12/2006 | Prosise | |
| 2007/0116748 A1 * | 5/2007 | Isele et al. | 424/443 |

FOREIGN PATENT DOCUMENTS

| | | |
|---|---|---|
| EP | 544440 A2 | 6/1993 |
| EP | 544490 A1 | 6/1993 |
| EP | 549272 A1 | 6/1993 |
| EP | 790244 A1 | 8/1997 |
| EP | 549271 B1 | 10/1997 |
| EP | 0811389 A1 | 10/1997 |
| EP | 0811390 A1 | 10/1997 |
| EP | 0811391 A1 | 10/1997 |
| EP | 0850617 A1 | 1/1998 |

(56) References Cited

FOREIGN PATENT DOCUMENTS

| | | |
|---|---|---|
| EP | 1017776 A1 | 7/2000 |
| EP | 1053732 A2 | 11/2000 |
| EP | 775127 B1 | 9/2003 |
| EP | 1017776 B1 | 12/2003 |
| EP | 1886698 A1 | 2/2008 |
| EP | 1017773 B1 | 3/2008 |
| JP | 1993-123358 A | 5/1993 |
| WO | WO-9425077 A1 | 11/1994 |
| WO | WO-9428102 A1 | 12/1994 |
| WO | WO-9513351 A1 | 5/1995 |
| WO | WO-9513352 A1 | 5/1995 |
| WO | WO-9513353 A1 | 5/1995 |
| WO | WO-9524173 A2 | 9/1995 |
| WO | WO-9640661 A1 | 12/1996 |
| WO | WO 98/26808 A2 | 6/1998 |
| WO | WO 99/04830 A1 | 2/1999 |
| WO | WO-9914296 A1 | 3/1999 |
| WO | WO-9914302 A1 | 3/1999 |
| WO | WO-0069382 A1 | 11/2000 |
| WO | WO-2005120594 A1 | 12/2005 |

OTHER PUBLICATIONS

Tobe-Buse, "Advances in Inorganic and Bioinorganic Mechanisms", *Department of Inorganic Chemistry*, vol. 2, pp. 1-94 (1983).

Williams et al., "Coordination Complexes of Cobalt", *Journal of Chemical Education*, vol. 66, Issue 12, pp. 1043-1045 (1989).

W.L. Jolly, "The Preparation of Chloropenta-Ammine Cobalt (III) Chloride, Nitropentaamminecobalt (III) Chloride, and Nitritopentaammine-Cobalt (III) Chloride", *Prentice-Hall*, pp. 461-463 (1970).

Jackman et al., "Synthesis of Transition-Metal Carboxylato Complexes", *Inorganic Chemistry*, vol. 18, No. 6, pp. 1497-1502 and 2023-2025 (1979).

Wierenga et al., "Synthesis and Characterization of Cobalt (III) Nicotine Acid Complexes", *Inorg. Chem.*, 21, pp. 2881-2885 (1982).

Basolo et al., "Mechanism of Substitution Reactions in Complex Ions. I. Kinetics of the Aquation and Hydrolysis of Some C-Substituted Acetatopentamminecobalt (III) Ions", *Journal of Physical Chemistry*, vol. 56, pp. 22-25 (1952).

International Search Report, PCT/IB2008/052857, mailed Mar. 19, 2009, 14 pages.

\* cited by examiner

DISPOSABLE ABSORBENT ARTICLE HAVING ODOR CONTROL SYSTEM

CROSS REFERENCE TO RELATED APPLICATION

This application claims the benefit of U.S. Provisional Application No. 60/961,029, filed Jul. 18, 2007, the substance of which is incorporated herein by reference.

FIELD OF THE INVENTION

The present invention relates to disposable absorbent articles which have an improved odor control system. Examples of such disposable absorbent articles include disposable underwear, disposable diapers (adult and baby) including pull-on diapers and training pants, disposable panties for menstrual use, and disposable absorbent pads including sanitary napkins.

BACKGROUND OF THE INVENTION

A wide variety of disposable absorbent articles are designed not only to be efficient in the absorption of body fluids such as urine, blood, menses and the like, but also to be sanitary and comfortable in-use, are known in literature. Disposable absorbent products of this type generally comprise a fluid-permeable topsheet material, an absorbent core (or a fluid storage layer), and a fluid-impermeable backsheet material. Various shapes, sizes and thicknesses of such articles have been explored in an attempt to make their use more comfortable and convenient.

Recently, research has been focused on the removal of unpleasant odors. Many body fluids have an unpleasant odor (or an malodor), or develop such an odor when in contact with air and/or bacteria for prolonged periods. Urine and/or other exudates absorbed into the absorbent article are converted to ammonia by urease produced by skin-flora, i.e., a group of normal microorganisms on the skin. This ammonia could become a source of unpleasant odors.

Many attempts have been made to suppress the development of unpleasant odors. One approach is to apply antimicrobial materials into the absorbent article. Antimicrobial materials and bactericides in general are chemical compositions that are used to prevent microbiological contamination and deterioration of products, materials, and systems. Such antimicrobial materials and bactericides effectively work for removal or reduction of unpleasant odors developed from disposable absorbent articles which have already absorbed body fluids. Another approach is to apply an odor absorbing material into the absorbent article. The odor absorbing material absorbs unpleasant odors when the unpleasant odors develop while it may not prevent microbiological contamination and deterioration of products. Further, a perfume may be used to mask the unpleasant odors when the unpleasant odors develop.

Each of these approaches is effective in suppressing the development of unpleasant odors or in masking the unpleasant odors even when the unpleasant odors develop. Each of these approaches, however, has each unique drawback. While a hydrogel forming material comprising polyacrylic acid is known to absorb unpleasant odors derived from urine and/or other body exudates, the hydrogel forming material does not provide benefits noticeably perceivable to consumers with respect to odor control. Therefore, an antimicrobial material or a perfume has been added to the absorbent article to further enhance the odor control of the absorbent article. However, just adding the antimicrobial material into the absorbent article may cause skin safety issues or dysfunction of the antimicrobial material if the disposition of the antimicrobial material is not appropriate. Further, the perfume may cause the user to perceive too strong smell of perfume or may rapidly vaporize to lose the masking effect of the unpleasant odor if the disposition of the perfume is not appropriate. None of prior art has identified an disposable absorbent article to effectively dispose the odor control system comprising an antimicrobial material, an odor masking material and an odor absorbing and/or adsorbing material in the disposable absorbent article.

Based on the foregoing, there is a need for a disposable absorbent article which has an effective disposition of the odor control system so that each of the odor control ingredients effectively works in the disposable absorbent article.

SUMMARY OF THE INVENTION

The present invention is directed to a disposable absorbent article. The absorbent article comprises a topsheet; a backsheet combined with the topsheet; a fluid storage layer disposed between the topsheet and the backsheet and adjacent to the backsheet; an intermediate layer disposed between the fluid storage layer and the topsheet. The intermediate layer has a body-facing surface and a garment-facing surface. The disposable absorbent article comprises an odor control system. The odor control system comprises an antimicrobial material disposed between the topsheet and the body-facing surface of the intermediate layer; an odor masking material disposed between the backsheet and the garment-facing surface of the intermediate layer; and an odor absorbing and/or adsorbing material disposed in the fluid storage layer. The antimicrobial material and the odor masking material are separated by the intermediate layer.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying a drawing and which like designations are used to designate substantially identical elements, and in which:

DETAILED DESCRIPTION OF THE INVENTION

All cited references are incorporated herein by reference in their entireties. Citation of any reference is not an admission regarding any determination as to its availability as prior art to the claimed invention.

Herein, "comprise" and "include" mean that other element(s) and step(s) which do not affect the end result can be added. These terms encompass the terms "consisting of" and "consisting essentially of".

Herein, "absorbent article" refers to devices which absorb and contain body exudates, and, more specifically, refers to devices which are placed against or in proximity to the body of the wearer to absorb and contain the various exudates discharged from the body. Herein, "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). One embodiment of the disposable absorbent article of the present invention is a unitary disposable diaper 20, shown in FIG. 1. Herein, "unitary" absorbent article refers to absorbent articles which are formed of separate parts united together to form a coordinated entity so that they do not require separate manipulative parts like a separate holder and liner. Herein, "diaper" refers to an absorbent article generally worn by infants and incontinent persons that is worn about the lower torso of the wearer. It should be understood, however, that the present invention is also applicable to other disposable absorbent articles such as disposable underwears, disposable diapers (adult and baby) including pull-on diapers and training pants, disposable panties for menstrual use, and disposable absorbent pads including sanitary napkins.

Figure 1:
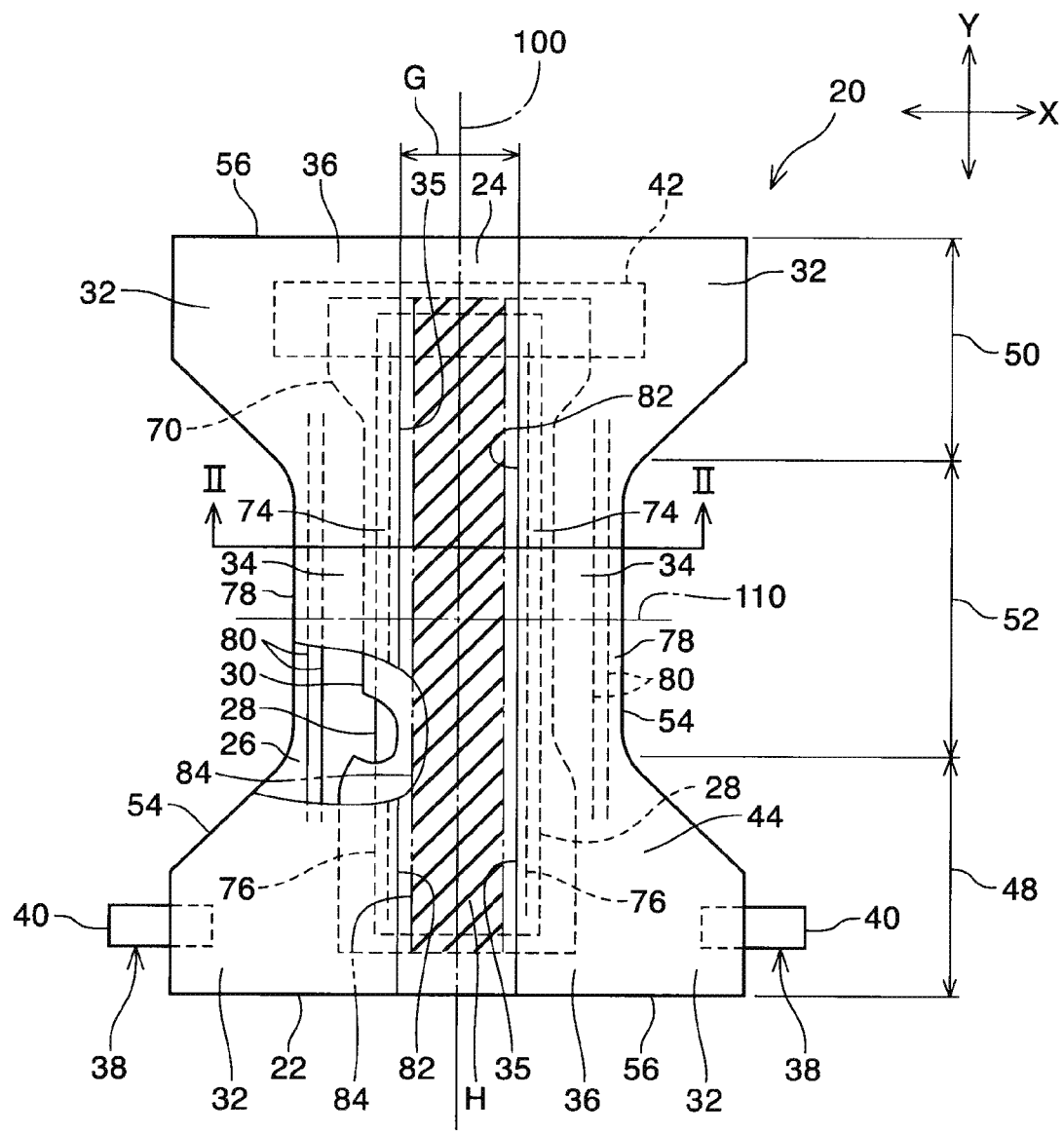
FIG. 1 is a simplified top plan view of one embodiment of the disposable absorbent article of the present invention in its flat uncontracted condition showing the body-facing side of the garment.
Figure 2:
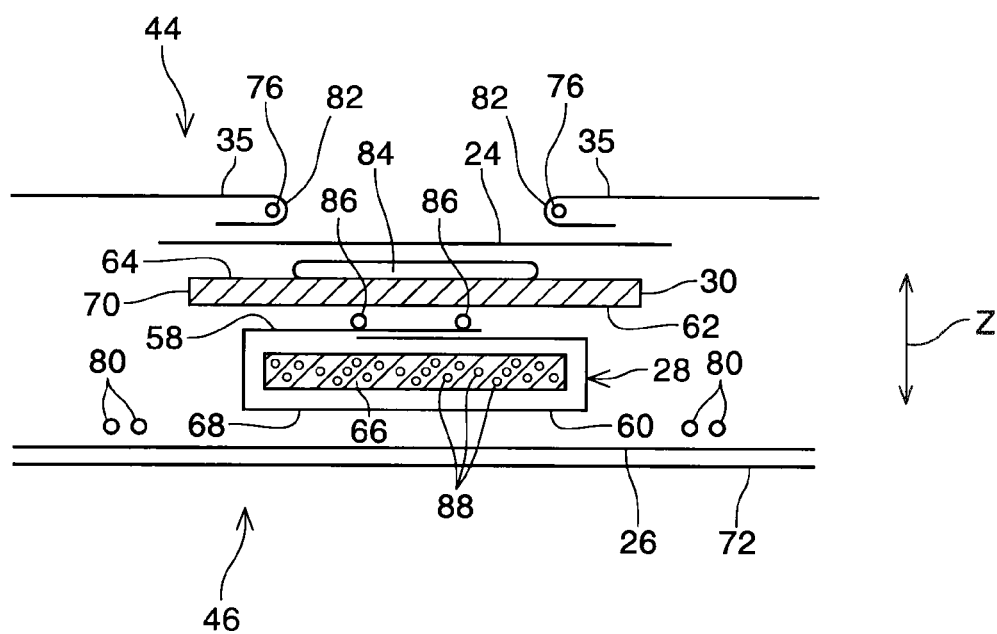
FIG. 2 is a simplified cross sectional view taken along the line II-II of FIG. 1 with various elements of the disposable absorbent article being unconnected.

FIG. 1 is a top plan view of the disposable diaper 20 in its flat-out, uncontracted state (i.e., with elastic induced contraction pulled out) with portions of the structure being cut-away to more clearly show the construction of the diaper 20 and with the portion of the diaper 20 which faces the wearer, the body-facing surface, facing the viewer. FIG. 2 is a cross sectional view taken along the line II-II of FIG. 1 with various elements of the diaper 20 being unconnected. As shown in FIG. 1, the diaper 20 comprises a chassis 22 comprising a liquid pervious topsheet 24; a liquid impervious backsheet 26 joined to the topsheet; a fluid storage layer 28 disposed between the topsheet 24 and the backsheet 26 and disposed adjacent to the backsheet 26; and an intermediate layer 30 disposed between the fluid storage layer 28 and the topsheet 24. The diaper 20 may further comprise side panels 32; elasticized leg cuffs 34 comprising inner barrier cuffs 35; elasticized waistbands 36; and a fastening system 38 comprising a pair of securement members 40 and a landing member 42.

The diaper 20 is shown in FIG. 1 to have a body-facing surface 44 (facing the viewer in Figure), a garment-facing surface 46 (refer to FIG. 2) opposed to the body-facing surface 44, a back region 48, a front region 50 opposed to the back region 48, a crotch region 52 positioned between the back region 48 and the front region 50, and a periphery which is defined by the outer perimeter or edges of the diaper 20 in which the side edges are designated 54 and the end edges are designated 56. The body-facing surface 44 of the diaper 20 comprises that portion of the diaper 20 which is positioned adjacent to the wearer's body during use (i.e., the body-facing surface 44 generally is formed by at least a portion of the topsheet 24 and other components joined to the topsheet 24). The garment-facing surface 46 comprises that portion of the diaper 20 which is positioned away from the wearer's body (i.e., the garment-facing surface 46 is generally formed by at least a portion of the backsheet 26 and other components joined to the backsheet 26). The back region 48 and the front region 50 extend from the end edges 56 of the periphery to the crotch region 52.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The fluid storage layer 28 may be any absorbent member which is generally compressible, conformable, non-irritating to the wearer's skin, and capable of absorbing and retaining liquids such as urine and other certain body exudates. As shown in FIG. 2, the fluid storage layer 28 has a garment-facing surface 58, a body-facing surface 60, a pair of side edges, and a pair of waist edges. The fluid storage layer 28 may be disposed between the topsheet 24 and the backsheet 26 and disposed adjacent to the backsheet 26. The fluid storage layer 28 may be directly disposed onto the backsheet 26 or indirectly disposed on the backsheet by inserting an additional material between the fluid storage layer 28 and the backsheet 26. The fluid storage layer 28 may be manufactured in a wide variety of sizes and shapes (e.g., rectangular, hourglass, "T"-shaped, asymmetric, etc.). The fluid storage layer 28 may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations thereof. In this embodiment, the fluid storage layer 28 comprises a generally rectangular fluid storage core 66 comprising airfelt and a superabsorbent material; and a core wrap 68 comprising a tissue covering the fluid storage core 66.

The intermediate layer 30 may be disposed between the topsheet 24 and the fluid storage layer 28 and disposed adjacent to the topsheet 24. The intermediate layer 30 may serve to isolate the fluid storage layer 28 from the body-facing surface 44 of the diaper 20 to reduce rewet, to provide the diaper 20 with a cushioning effect, to acquire and transport body fluids from the body-facing surface 44 of the diaper. An additional material may be inserted between the intermediate layer 30 and the topsheet 24 and/or between the intermediate layer 30 and the fluid storage layer 28. The intermediate layer 30 has a garment-facing surface 62 and a body-facing surface 64. The intermediate layer 30 may be manufactured in a wide variety of sizes and shapes (e.g., rectangular, hourglass, "T"-shaped, asymmetric, etc.). The intermediate layer 30 may include creped cellulose wadding; meltblown polymers, including coform; chemically stiffened, modified or cross-linked cellulosic fibers; nonwoven comprising a polymeric fibers; tissue, including tissue wraps and tissue laminates; absorbent foams; absorbent sponges; superabsorbent polymers; absorbent gelling materials; or any other known absorbent material or combinations thereof. In this embodiment, the intermediate layer 30 serves to acquire and transport body fluids from the body-facing surface 44 of the diaper into the fluid storage layer 28, and comprises a generally hourglass-shaped acquisition layer 70 comprising airfelt. Alternatively, a nonwoven material comprising polymeric fibers may be used as an intermediate layer to enhance the acquisition/transportation speed of body fluids and rewet effect. In the embodiment shown in FIG. 1, the intermediate layer 30 is generally hourglass-shaped and is longer in the longitudinal direction and wider in the lateral direction than the fluid storage layer 28.

The topsheet 24 is positioned adjacent the body-facing surface 64 of the intermediate layer 30 and is joined thereto and to the backsheet 26 by attachment means (not shown) such as those well known in the art. In one embodiment, the topsheet 24 and the backsheet 26 are joined directly to each other in the diaper periphery.

The topsheet 24 may be compliant, soft feeling, and non-irritating to the wearer's skin. Further, the topsheet 24 may be liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The backsheet 26 is that portion of the diaper 20 which is generally positioned away from the wearer's skin and which prevents the exudates absorbed and contained in the fluid storage layer 28 from wetting articles which contact the diaper 20 such as bedsheets and undergarments. Thus, the backsheet 26 may be impervious to liquids (e.g., urine) and may be manufactured from a thin plastic film or a liquid impervious nonwoven, although other flexible liquid impervious materials may also be used. (As used herein, the term "flexible" refers to materials which are compliant and will readily conform to the general shape and contours of the human body.) However, the backsheet 26 may permit vapors to escape from the diaper 20. A suitable material for the backsheet 26 is a thermoplastic film having a thickness of from about 0.012 mm to about 0.051 mm, which may comprise polyethylene or polypropylene. The backsheet 26 may be positioned adjacent the garment-facing surface 60 of the fluid storage layer 28. The backsheet 26 may be joined to the fluid storage layer 28 and/or the topsheet 24 by any suitable attachment means known in the art such as an adhesive, heat bonds, pressure bonds, ultrasonic bonds, dynamic mechanical bonds, or combinations of these attachment means.

The diaper 20 may further comprise an outer cover 72 joined with at least a portion of the garment-facing surface of the backsheet 26 to form a laminate. The outer cover may comprise a nonwoven material. The outer cover may cover all or substantially all of the garment-facing surface of the backsheet 26, or may cover only discrete predetermined portions. In one embodiment, the nonwoven material of the outer cover covers all or substantially all of the backsheet 26 in order to provide the diaper 20 with a cloth-like look and feel.

Figure 3:
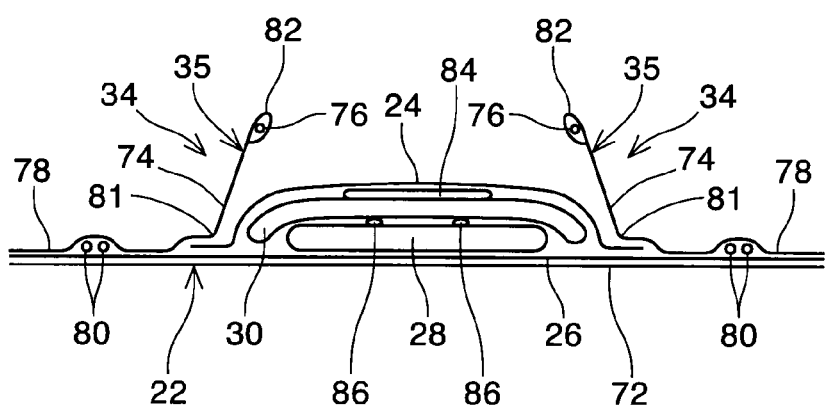
FIG. 3 is a simplified cross sectional view taken along the line II-II of FIG. 1 with various elements of the disposable absorbent article being connected and inner barrier cuffs standing up.

The diaper 20 may further comprise elasticized leg cuffs 34 for providing improved containment of liquids and other body exudates. The entirety or a portion of the elasticized leg cuffs 34 may be hydrophobic. The hydrophobic nature of the elasticized leg cuffs 34 is desired to prevent body fluids from passing through the elasticized leg cuffs 34. Each elasticized leg cuff 34 may comprise at least a hydrophobic inner barrier cuff 35 comprising a barrier flap 74 and a spacing element 76. In the embodiment shown in FIG. 1 where the diaper 20 is in its flat-out, uncontracted state, the barrier flap 74 lies down on the topsheet 24. In one embodiment, the elasticized leg cuff 34 additionally comprises an elastic gasketing cuff 78 with one or more elastic strands 80, positioned outboard of the inner barrier cuff 35. Further, the inner barrier cuff 35 has a proximal edge 81 and a distal edge 82. The distal edge 82 of the inner barrier cuff 35 is that part of the elasticized leg cuff 32 which is spaced away from the chassis 22 of the diaper 20 by the spacing element 76 when the diaper 20 is being worn (refer to FIG. 3). The proximal edge 81 is that part of the inner barrier cuff 35 which is joined to the chassis 22 of the diaper 20. The proximal edge 81 is generally located laterally inboard of the periphery of the diaper 20.

It may also be desirable to provide the diaper 20 with extensibility or elasticity in all or a portion of the side panels 32. Extensible side panels 32 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 32 further provide more effective application of the diaper 20 since even if the diaperer pulls one side panel 32 farther than the other during the application (asymmetrically), the diaper 20 will "self-adjust" during wear.

The diaper 20 may further comprise an elasticized waistband 36 that provides improved fit and containment. The elasticized waistband 36 is that portion or zone of the diaper 20 which is intended to elastically expand and contract to dynamically fit the wearer's waist. The diaper 20 is constructed so as to have two elasticized waistbands 36, one positioned in the back region 48 and one positioned in the front region 50, although the diaper 20 can be constructed with a single elasticized waistband. The diaper 20 additionally comprises a waist cap to enhance containment.

The diaper 20 also comprises a fastening system 38 which forms a side closure which maintains the back region 48 and the front region 50 in an overlapping configuration such that lateral tensions are maintained around the circumference of the diaper to maintain the diaper on the wearer.

The diaper 20 comprises the odor control system which may comprise a three-step process. The three-step process comprises (1) an odor generation control process, (2) an odor diffusion control process, and (3) an odor masking process.

The odor generation control process includes the use of antimicrobial material. Herein, "antimicrobial material" (hereinafter referred to as "AMM") encompasses an ingredient which can reduce the number of microbes or prevent the growth of microbes, such as bacteria, fungi, viruses, or parasites in disposable absorbent articles. It has been known that urine and/or other exudates absorbed into the fluid storage layer 28 of the diaper 20 are converted to ammonia by microbes. Microbes initially reside on the human body surface, and moves from the human body surface into the diaper 20 such as the fluid storage layer 28 through the intermediate layer 30 by being washed off by body fluids. When body fluids contact microbes for prolonged periods in the diaper 20, ammonia which is a source of unpleasant odor is generated. The AMM is useful in preventing the growth of microbes in the diaper 20 or in reducing the number of microbes in the diaper 20. The AMM may be disposed in a portion of the diaper 20 as close to the human body as possible such as on the body-facing surface of the topsheet 24 so that the AMM effectively functions against microbes which move from the human body surface into the diaper 20. However, the AMM may cause skin safety problems when it is disposed on the body-facing surface of the topsheet 24. Therefore, the AMM may be disposed between the topsheet 24 and the body-facing surface 64 of the intermediate layer 30 so that the AMM effectively functions against microbes and reduces skin problems.

The odor diffusion control process includes the use of odor absorption and/or adsorption material. Herein, "odor absorption and/or adsorption material" (hereinafter referred to as "OAM") encompasses an ingredient which can prevent or reduce diffusion of an unpleasant odor if the unpleasant odor is generated. The OAM is able to absorb or adsorb an unpleasant odor. While the AMM should be able to effectively control odor generation by microbes, there could be still odor generation. The OAM is used to control odor diffusion in case an unpleasant odor is generated. As explained above, body fluids are stored into the fluid storage layer 28 and microbes also move into the fluid storage layer 28 with the body fluids. Therefore, the OAM may be disposed in the fluid storage layer 28 so that the OAM effectively absorbs or adsorbs the unpleasant odor generated at the source of odor generation.

The odor masking process includes the use of odor masking material. Herein, "odor masking material" (hereinafter referred to as "OMM") encompasses an ingredient which can mask an unpleasant odor so that the wearer of the diaper 20 or the caregiver does not sense the unpleasant odor or at least becomes less sensitive to the unpleasant odor if the unpleasant odor is generated and diffused. The OMM is useful when the unpleasant odor is generated by the remaining microbes which have not been eradicated by the AMM and is diffused into the air without being absorbed and/or adsorbed by the OAM. The OMM helps the wearer of the diaper 20 or the caregiver not sense the unpleasant odor or at least becomes less sensitive to the unpleasant odor. The OMM may, however, easily vaporize if it is disposed close to the surface of the diaper 20, which prevents the OMM from a prolonged masking effect. On the other hand, the OMM may not effectively function if it is disposed close to the bottom of the diaper 20. Therefore, the OMM may be disposed between the backsheet 26 and the garment-facing surface 62 of the intermediate layer 30. The intermediate layer 30 prevents the OMM from rapidly vaporizing before the OMM needs to function as required, but help a gradual vaporization of the OMM so that the masking effect lasts for a period of expected product use.

Absence of any part of the odor control system will result in experience of the unpleasant odor when in the actual product usage. For example, when the diaper does not comprise the AMM, ammonia may be easily generated with microbes under prolonged product usage. As a result, absorption and/or adsorption function of the OAM is saturated, and ammonia eventually freely vaporizes into the air. Then the concentration of ammonia in the air increases, and eventually exceeds the masking efficacy of the OMM, resulting in experiencing the unpleasant odor. Another example is when the diaper does not comprise the OAM, the remaining microbes which were not eradicated by the AMM continue generating ammonia, which freely vaporizes into the air. The concentration of the ammonia in the air eventually exceeds the masking efficacy of the OMM, resulting in experiencing the unpleasant odor. Also, when the diaper does not comprise the OMM, the sensitive human nose will capture the unpleasant odor from the remaining ammonia, which are generated by the remaining microbes and vaporizes without being absorbed and/or adsorbed by the OAM.

The AMM useful in the present invention may include any antimicrobial substances which include germicides, antibiotics, antibacterials, antivirals, antifungals, antiprotozoals and antiparasites. Known antimicrobial substances comprise alcohols, aldehydes, phenols, hydrogen peroxides, chlorines, hypochlorites, or surfactants.

The AMM may include, but are not limited to, organic surfactants which are chemical compounds possessing both hydrophilic and hydrophobic properties, and are usually known as amphiphilic surfactants. Amphiphilic surfactants are effective in reducing the number of microbes or preventing the growth of microbes. Amphiphilic surfactants may include cationic surfactants, zwitterionic surfactants, and mixtures thereof. Cationic surfactant contains the positively charged groups in its hydrophilic head, and zwitterionic surfactant contains a head with two oppositely charged groups.

Cationic surfactants may include quaternary ammonium cations, a.k.a quats, such as cetyl trimethylammonium bromide (CTAB), cetyl trimethylammonium chloride, didodecyl dimethylammonium chloride, other alkyltrimethylammonium salts, cetylpyridiniumammonium chloride, polyethoxylated tallow amine (POEA), benzalkonium chloride (BAC), and benzethonium chloride (BZT).

Zwitterionic surfactants may include dodecyl betaine, dodecyl dimethylamine oxide, cocamidopropyl betaine, coco ampho glycinate, alkyl diaminoethylglicyne hydrochloric acid, and alkyl polyaminoethylglycine hydrochloric acid.

In one embodiment, the AMM may be quaternary ammonium cations among cationic surfactants, or zwitterrionic surfactant with amino acid as ionic groups, and mixtures thereof.

The quaternary ammonium cation may be effective in reducing the number of microbes or preventing the growth of microbes represented by the minimum inhibitory concentration (MIC). Without wishing to be bound by the theory, the mechanism can be explained as follows. When the quaternary ammonium cations are solved in water, the ammonium group is positively charged. Because the proteins of the microbes are negatively charged, the positively charged quaternary ammonium cations are attached to the cell membrane of the microbes with electric interaction. Then, the attached quaternary ammonium is penetrated into the cell membrane of the microbes with its hydrophobic groups, and affects to the physiological activities, leading eventual death of the microbe.

The AMM 84 may be disposed anywhere in the Z-direction of the diaper 20 between the topsheet 24 and the body-facing surface 64 of the intermediate layer 30. Herein, the term "Z-direction" means the thickness direction of the diaper 20 as shown in FIG. 2. For example, the AMM 84 may be directly disposed on the garment-facing surface of the topsheet 24, or on the body-facing surface 64 of the intermediate layer 30. Alternatively, the AMM 84 may be disposed on a carrier means such as a nonwoven, a tissue, or other absorbent members which is interposed between the topsheet 24 and the intermediate layer 30. In the embodiment shown in Figures, the AMM 84 is applied as an aqueous solution onto the body-facing surface 64 of the intermediate layer 30 and therefore is directly disposed thereon.

The AMM 84 may be disposed in any portion in the X-Y direction of the diaper 20. Herein, the term "X-Y direction" means the direction parallel to the plane perpendicular to the Z-direction of the diaper 20 as shown in FIG. 1. Microbes initially reside on human body surfaces. Microbes are washed off by body fluids and transported together with body fluids from the human body surface to the portion of the diaper which could be potentially insulted by body fluids. Body fluids such as urine could be degraded by microbes in a portion of the diaper where body fluids are transported to generate ammonia which could be a source of unpleasant odor. The AMM 84, therefore, may be disposed in a portion of the diaper 20 in the X-Y direction which could be potentially insulted by body fluids. The AMM 84 may be disposed in a portion of the X-Y direction of the diaper 20 corresponding to a portion between the proximal edge 81 of the inner barrier cuff 35 since such a portion of the diaper 20 is the lateral maximum extent of the diaper 20 in which body fluids could be transported. The AMM 84 may be disposed in a portion of the X-Y direction of the diaper 20 corresponding to a portion between the end edges 56 of the diaper 20 since such a portion of the diaper 20 is the longitudinal maximum extent of the diaper 20 in which body fluids could be transported. The AMM 84 may be also disposed in a portion of the X-Y direction of the diaper 20 corresponding to the entire portion or a portion of the intermediate layer 30.

One of the AMM 84 may comprise amphiphilic surfactants as stated above. The disposition of such AMM 84 comprising amphiphilic surfactants may be restricted so that amphiphilic property of the AMM 84 does not interfere the function of the diaper 20. For example, the inner barrier cuff 35 is hydrophobic in order to prevent body fluids from leaking through the inner barrier cuff 35. However, amphiphilic surfactants 84 may migrate, e.g., with body fluids, and may reach the hydrophobic inner barrier cuff 35. The hydrophobic groups in the amphiphilic surfactants 84 interact with and adhere to the hydrophobic inner barrier cuff 35. As a result, the hydrophilic groups of the amphiphilic surfactants 84 transform the hydrophobic nature of the inner barrier cuff 35 to the hydrophilic nature. Amphiphilic surfactants 84, therefore, are desired not to contact the hydrophobic inner barrier cuff 35. The inner barrier cuff 35 stands up towards the wearer's body when in use of the diaper 20. However, the inner barrier cuff 35 is placed onto the topsheet 24 in the folded configuration of the diaper 20 to form a gap G (refer to FIG. 1) in the lateral direction of the diaper between the distal edge 82 of each of the inner barrier cuffs 35 before use of the diaper 20, e.g., when the diaper is contained into the package. In such a folded configuration, amphiphilic surfactant 84 is disposed in a portion of the diaper 20, which is shown as a hatching area H in FIG. 1, corresponding to the gap G and is not positioned in a portion of the diaper 20 corresponding to the area where the folded inner barrier cuff 35 is folded so that the amphiphilic surfactant 84 does not contact the hydrophobic inner barrier cuff 35.

The diaper 20 may comprise the AMM of not less than about 0.035 g/m$^2$. When the AMM amount is less than about 0.035 g/m$^2$, the AMM may not effectively reduce the number of the microbes or does not effectively prevent the growth of microbes. The more amount of AMM the diaper 20 has, the more efficacy the diaper 20 provides in reducing the number of the microbes and in preventing the growth of microbes. Therefore, while the upper limit of the amount of AMM can be arbitrary, the upper limit may practically determined from the viewpoints of AMM cost and/or skin safety.

The AMM 84 may be applied to the diaper 20 by any known methods. In one embodiment, the AMM 84 can be applied as aqueous solution. The aqueous solution enables the AMM 84 to be applied with small quantity beyond the minimum pump capability, and enables the AMM 84 to be applied with stable quantity between diapers. The aqueous solution of the AMM 84 is prepared by the following procedure: 1) measure the required quantity of the AMM 84, 2) add the AMM 84 to the mixer, 3) measure the required quantity of water, 4) add the water to the mixer, and 5) mix the AMM 84 and water until the solution is fully mixed in the mixer. The concentration of the applied AMM 84 solution may be less than about 10%. Further, the concentration of the applied AMM 84 in the solution can be from about 3% to about 5%.

The OMM 86 is typically a perfume which is a mixture of fragrant essential oils and aroma compounds, fixatives, and solvents used to give the human body, objects, and living spaces a pleasant smell. The OMM 86 may be prepared to be used for human body. In one embodiment, perfume is chosen from categories of floral, soft floral, floral oriental, soft oriental, oriental, woody oriental, wood, mossy woods, dry woods, citrus, fresh, green, water, fougere, fruity, and powdery, and mixture of thereof. The perfume can be floral, citrus, fruity, green, powdery, and mixture of thereof.

The OMM 86 may be disposed anywhere in the Z-direction of the diaper 20 between the backsheet 26 and the garment-facing surface 62 of the intermediate layer 30. For example, the OMM 86 may be directly disposed on the garment-facing surface 62 of the intermediate layer 30, on the body-facing surface 58 of the fluid storage layer 28, on the garment-facing surface 60 of the fluid storage layer 28, or on the body-facing surface of the backsheet 26. The OMM 86 may be disposed inside the fluid storage layer 28. Alternatively, the OMM 86 may be disposed on a carrier means such as a nonwoven, a tissue, or other absorbent members which is interposed between the garment-facing surface 62 of the intermediate layer 30 and the backsheet 26. In the embodiment shown in FIG. 2, the OMM 86 is applied as an aqueous solution onto the body-facing surface 58 of the fluid storage layer 28 and therefore is directly disposed thereon. The OMM 86 may be disposed in any portion in the X-Y direction of the diaper 20 as far as it is disposed between the backsheet 26 and the garment-facing surface 62 of the intermediate layer 30 in the Z-direction of the diaper 20.

The diaper 20 may comprise the OMM of between about 0.008 g/pad and about 0.03 g/pad. When the OMM amount is less than about 0.008 g/pad, the OMM may not provide a desired effect of masking an unpleasant odor and the OMM will easily vaporize in a short period to lose the masking effect. When the OMM amount is more than about 0.03 g/pad, the OMM may give the user too strong smell and the user could perceive it an unpleasant odor.

The OMM 86 may be applied to the diaper 20 by any known methods. In one embodiment, the OMM 86 is mixed with a surfactant, solved in water, and applied to the diaper 20. In the embodiment shown in FIG. 2, the OMM 86 may be applied onto the fluid storage layer 28 as two lines of continuous beads of aqueous solution which continuously extend along the longitudinal direction of the diaper 20. The aqueous solution enables the OMM 86 to be applied with small quantity beyond the minimum pump capability, and enables the OMM 86 to be applied with uniform quantity on a diaper and with stable quantity between diapers. The surfactant is chosen from any known solubilizers or emulsifiers to effectively enables the aqueous solution.

The aqueous solution of the OMM 86 is prepared by the following procedure: 1) measure the required quantity of the OMM 86, 2) add the OMM 86 to the mixer, 3) measure the required quantity of a surfactant, 4) add the surfactant to the mixer, 5) measure the required quantity of water, 6) add the water to the mixer, and 7) mix the OMM 86, the surfactant and water until the solution is fully mixed in the mixer. The concentration of the applied OMM 86 in the solution may be from about 5% to about 15%. The concentration of the applied OMM 86 in the solution can be from about 6% to about 8%. The concentration of the added surfactant in the solution may be from about 0.1% to about 30%. The concentration of the surfactant in the solution can be from about 0.5% to about 25%.

The OMM 86 may be applied to the diaper 20 as aqueous solution by solubilized to water using a surfactant. As a result, one embodiment of the diaper 20 may comprise two types of surfactants which are surfactant as the AMM 84 and surfactant used for solubilizing or emulsifying the OMM 86. As mentioned above, the effective AMM 84 can be quaternary ammonium cations. However, the antimicrobial efficacy of the quaternary ammonium cations is known to decrease with existence of other surfactants or organic chemical because of chemical interactions between the surfactants. Also, it is known that the solubility of the quaternary ammonium cations decreases and quaternary ammonium cations precipitate under existence of other surfactants. Therefore, the AMM 84 solution should not be mixed with the OMM 86 solution when they are prepared and applied to the diaper 20. If the AMM 84 solution is mixed with the OMM 86 solution in the preparation, the solubility of the AMM 84 decreases and the AMM 84 precipitates, which results in quantity variation of the AMM 84 applied on diapers. Further, the AMM 84 and the OMM 86 should not exist at the same location in the diaper 20 in order to keep the antimicrobial efficacy of the AMM 84 because the OMM 86 is a mixture of organic chemicals and the OMM 86 solution comprises a surfactant. Both of them decrease the antimicrobial efficacy of the AMM 84. In the embodiment of the present invention, therefore, the AMM 84 and the OMM 86 are separated by the intermediate layer 30 in the Z-direction of the diaper 20.

The OAM 88 may include any chemical compound capable of absorbing and/or adsorbing an unpleasant odor contained in body fluids or generated when such body fluids are in contact with bacteria for prolonged periods.

The OAM 88 may include, but are not limited to, activated carbons, zeolite, polyacrylic acids, polyphenols, cyclodextrin, and mixture of thereof. In one embodiment, the OAM 88 may comprise a polyacrylic acid which is known as a hydrogel forming material to absorb liquid from a human body and to store in the diaper 20. The polyacrylic acids can absorb approximately 10 to 100 times more weight of the liquid than their own weight, and still can absorb the odor molecules.

The OAM 88 may be disposed in the fluid storage layer 28. For example, the OAM 88 may be disposed on the body-facing surface 58 or the garment-facing surface 60 of the fluid storage layer 28. Alternatively, the OAM 88 may be dispersed into the fluid storage layer 28 as in the embodiment shown in FIG. 2.

In one embodiment, the OAM 88 may be disposed from about 1% to about 50% weight of the diaper 20 in order to provide functions of sufficient liquid absorption and odor absorption and/or adsorption. The OAM 88 can be disposed from about 5% to about 35% weight of the diaper 20.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a topsheet;
   a backsheet;
   a fluid storage layer disposed between the topsheet and the backsheet and adjacent to the backsheet, wherein the fluid storage layer has a body-facing surface and a garment-facing surface;
   an intermediate layer disposed between the fluid storage layer and the topsheet, the intermediate layer having a body-facing surface and a garment-facing surface;
   an odor control system comprising an antimicrobial material disposed between the topsheet and the body-facing surface of the intermediate layer;
   an odor masking material disposed between the garment-facing surface of the intermediate layer and the body-facing surface of the fluid storage layer;
   an odor absorbing and/or adsorbing material disposed in the fluid storage layer;
   wherein the antimicrobial material and the odor masking material are separated by the intermediate layer; and
   wherein the disposable absorbent article further comprises a pair of hydrophobic inner barrier cuffs, each inner barrier cuff having a proximal edge and a distal edge provided with a spacing element so that the inner barrier cuff stands up towards the wearer's body when in use of the absorbent article, the inner barrier cuff being placed onto the topsheet before use of the absorbent article to form a gap between the distal edge of each of the inner barrier cuffs, wherein the antimicrobial material is positioned in a portion of the absorbent article corresponding to the gap between the distal edge of each of the inner barrier cuffs and is not positioned in a portion of the absorbent article corresponding to the area where the folded inner barrier cuff is folded before use of the absorbent article.

2. The disposable absorbent article of claim 1 wherein the antimicrobial material comprises an amphiphilic surfactant applied to the absorbent article as an aqueous solution.

3. The disposable absorbent article of claim 2 wherein the aqueous solution of the antimicrobial material is applied on the body-facing surface of the intermediate layer.

4. The disposable absorbent article of claim 1 wherein the absorbent article comprises of not less than about 0.035 g/m$^2$ of the antimicrobial material.

5. The disposable absorbent article of claim 1 wherein the absorbent article comprises between about 0.008 g/pad and about 0.03 g/pad of the odor masking material.

6. The disposable absorbent article of claim 1 wherein the odor masking material is solubilized with surfactant into water and is applied to the absorbent article as an aqueous solution.

7. The disposable absorbent article of claim 6 wherein the fluid storage layer has a body-facing surface and a garment-facing surface, and wherein the aqueous solution of the odor masking material is applied on the body-facing surface of the fluid storage layer.

8. The disposable absorbent article of claim 1 wherein the odor absorbing and/or adsorbing material comprises a hydrogel forming material comprising polyacrylic acid.

9. The disposable absorbent article of claim 1 wherein the odor masking material is disposed on the body-facing surface of the backsheet.

* * * * *